United States Patent [19]

Ruiter

[11] Patent Number: 4,922,918
[45] Date of Patent: May 8, 1990

[54] AUTOMATIC NON-INVASIVE BLOOD PRESSURE READING DEVICE

[75] Inventor: Karl A. Ruiter, La Canada, Calif.

[73] Assignee: Medical Data Electronics, Inc., Arleta, Calif.

[21] Appl. No.: 339,307

[22] Filed: Apr. 17, 1989

[51] Int. Cl.⁵ .............................................. A61B 5/02
[52] U.S. Cl. ..................................... 128/681; 128/680
[58] Field of Search ........................ 128/672, 677–686

[56] References Cited

U.S. PATENT DOCUMENTS

| | | |
|---|---|---|
| 3,903,872 | 9/1975 | Link . |
| 4,009,709 | 3/1977 | Link et al. . |
| 4,174,707 | 11/1979 | Link et al. . |
| 4,360,029 | 11/1982 | Ramsey, III .......................... 128/681 |
| 4,367,751 | 1/1983 | Link et al. . |
| 4,427,013 | 1/1984 | Nunn et al. . |
| 4,461,266 | 7/1984 | Hood, Jr. et al. ..................... 128/681 |
| 4,517,986 | 5/1985 | Bilgutay . |
| 4,543,962 | 10/1985 | Medero et al. ................... 128/680 X |
| 4,546,775 | 10/1985 | Medero ............................ 128/680 X |
| 4,638,810 | 1/1987 | Ramsey, III et al. ................ 128/681 |
| 4,699,152 | 10/1987 | Link . |
| 4,729,383 | 3/1988 | Susi ................................. 128/680 X |
| 4,777,959 | 10/1988 | Wallach et al. .................. 128/680 X |
| 4,793,360 | 12/1988 | Miyawaki et al. ................... 128/681 |

Primary Examiner—Angela D. Sykes
Attorney, Agent, or Firm—Lyon & Lyon

[57] ABSTRACT

An improved method and apparatus for non-invasive determination of blood pressure is disclosed. The oscillometric technique is employed, wherein a valve representative of the blood pressure is derived from a signal representative of the pressure oscillations in a cuff, where the value is derived for a plurality of cuff pressures, and where the cuff pressure corresponding to the maximum of the values derived from the pressure oscillations is taken to be the mean arterial pressure. The instant method uses as the value the complementary oscillation index which is defined to be the area bounded by a line connecting successive peaks in the signal and the signal beneath the line, divided by the time between peaks. Apparatus employing both digital and analog circuitry is employed.

7 Claims, 6 Drawing Sheets

TYPICAL OSCILLATION ENVELOPES

FIG_4B

AUTOMATIC NON-INVASIVE BLOOD PRESSURE READING DEVICE

FIELD OF THE INVENTION

This invention relates in general to the field of blood pressure measuring devices, and in particular to non-invasive blood pressure measuring devices which operate by oscillometry.

BACKGROUND OF THE INVENTION

The need to accurately, reliably and easily determine a patient's blood pressure has long been recognized as a goal. Typically, the blood pressure varies with time in a series of irregularly shaped pulses. The diastolic pressure is the baseline pressure for these pulses. The systolic pressure is defined to be the peak pressure for these pulses. Another useful measure of the pressure is the mean arterial pressure, that is, the time weighted average of the pulses. Ordinarily, the mean arterial pressure is not the arithmetic average of the systolic and diastolic pressures, but rather, is lower than the arithmetic average because the pulses tend to be weighted towards the bases than the peaks.

Various methods have been known to the art for determining blood pressure. Broadly, measurement methods may be categorized as either intrusive or non-intrusive. Intrusive blood pressure measuring devices are inserted directly into the blood vessel to make blood pressure measurements. While this method provides accurate blood pressure measurements, it tends to be somewhat painful and requires the attention of a skilled operator.

Non-invasive methods can provide useful measures of the blood pressure with no intrusion into the body. In the auscultatory method, a pressurizable cuff is placed around the upper arm of the patient and inflated to a pressure above the systolic pressure. This stops the flow of blood in the underlying artery. The cuff pressure is slowly decreased and a stethoscope or microphone is used to listen for Korotokoff sounds which accompany the resumption of blood flow in the artery. The systolic pressure is taken to be the cuff pressure at which the sounds are first heard and the diastolic pressure is taken to be the cuff pressure at which the sounds disappear. The auscultatory method provides an easy, inexpensive way to determine the systolic and diastolic pressure of a patient. This method tends not to be very precise, and does not directly provide a measure of the mean arterial pressure.

Figure 1A:
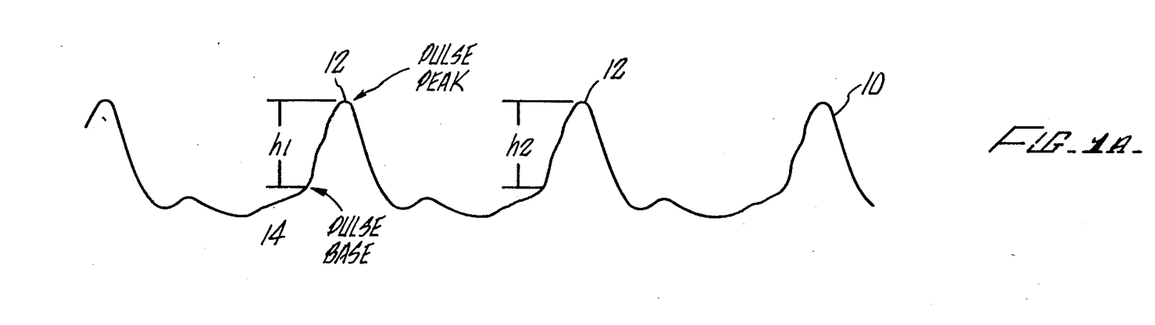
FIG. 1A shows a graphic representation of oscillation pressure with respect to time relative to the Base to Peak measurement method.

Another noninvasive method is termed the oscillometric method. The oscillometric method monitors the oscillations in pressure in an inflatable cuff which are caused by variations in the arterial pressure. FIG. 1 shows a graphic representation of a normal oscillation pulse 10. The relative magnitude of the oscillations in cuff pressure are used to estimate the blood pressure. Parameters of the oscillations 10 considered relevant by the prior art included the pulse peak points 12, the pulse base 14 pressure and the lower peak 16 pressure. In the method known as the 'Base to Peak' method, the pressure differential between the pressure pulse peak 12 and the pressure at the pulse base 14 (labeled $h_1$ and $h_2$) was measured in a variety of prior art methods. (see e.g., the note here to fill in prior art.) Ordinarily, this pressure differential would be measured at a variety of cuff pressures. The cuff pressure could be changed either continuously or incrementally. The mean arterial pressure is usually taken to be the cuff pressure at which the oscillation magnitude is greatest. For example, in the base to peak method, that point would be when the pressure differential between the pulse peak 12 pressure and pulse base 14 pressure is maximized with respect to cuff pressure. The systolic pressure is usually taken to be the cuff pressure above mean arterial pressure at which the oscillation magnitude is a fixed percentage or fraction of the oscillation magnitude at mean arterial pressure. The diastolic pressure is usually taken to be the pressure below the mean arterial pressure at which the oscillation magnitude has dropped to a fixed percentage or fraction of the oscillation magnitude at the mean arterial pressure.

An alternative measurement of the oscillation 10 in cuff pressure is termed the 'Peak to Peak' value. In this method, the pressure differential between the value at the pulse peak 12 and the lower peak 16 is determined. Those pressure differentials are labeled as $a_1$ for the first cycle shown in FIG. 1B, and $a_2$ for the second cycle shown. See, e.g., U.S. Pat. Nos. 4,360,029 and 4,394,034 by Maynard Ramsey, III, and 4,461,266 by Hood.

The reliability and repeatability of these methods hinges on their ability to accurately determine oscillation magnitude. There are several barriers to accurate and reliable oscillation magnitude determination. First, artifacts caused by patient motion and other effects are nearly always present. These artifacts are superimposed upon the desired oscillation signal, causing it to be distorted. Second, many of the properties of the desired oscillation signal are not consistent from patient to patient, or even from oscillation to oscillation for a given patient. One factor which affects the consistency of these properties would include irregular heart rate.

The prior art methods which follow the Base to Peak or Peak to Peak methods have employed a variety of schemes to improve the accuracy and the reliability of the methods. Most often, the schemes involve artifact detection and rejection. Examples of artifact rejection algorithms can be seen for example in the U.S. Pat. Nos. 4,360,029 and 4,394,034 by Maynard Ramsey, III (artifact rejection algorithms look at, inter alia, select parameters such as peak height or time rate of change of successive samples or series of samples), 4,546,775 by Medero (rejection is signal slope is uncharacteristic of true complex). These techniques will accept only pulses with certain properties, such as specific rise times, or certain consistencies, such as consistent time between oscillations. While these techniques may work well in some cases, they may fail in other cases. Such artifact rejection schemes tend not to work well with very old or very ill patients, as such properties or consistencies may simply not be present. In these cases, these prior methods can yield unreliable measurements of blood pressure or no measurement at all.

Another disadvantage of the prior techniques is that the artifact rejection procedures often require a series of measurements to determine whether consistency is present. The more repetition of tests or measurements which are necessary increases the overall time for the blood pressure determination.

SUMMARY OF THE INVENTION

In the preferred method of the present invention, the oscillometric technique is employed to measure the oscillations in cuff pressure These oscillations are measured by computing the ratio of the area swept out above two successive oscillation peaks to the time between the oscillation peaks. In the preferred embodiment, the area measured is that bounded by a straight line connecting the two successive peaks and the oscillation signal. This is termed the summed complimentary oscillation value. The result of dividing the summed complimentary oscillation value by the time between the peaks is termed the complimentary oscillation index. The complimentary oscillation index is then determined for different cuff pressures. In the preferred embodiment, the cuff pressure is decremented in steps.

As the complimentary oscillation index is determined for different average cuff pressures, an oscillation envelope consisting of the oscillation index as a function of mean cuff pressure is compiled. The shape of the oscillation envelope is matched against an expected envelope shape. If a value of the oscillation envelope is found not to match the expected shape, the cuff is reinflated to the pressure of mismatch and the oscillation magnitude is rechecked. When a satisfactory oscillation envelope has been determined, the mean arterial pressure is taken to be the cuff pressure at which the complimentary oscillation index is a maximum. The systolic and diastolic pressures are set to be the cuff pressures at which the complimentary oscillation index is a predetermined percentage or fraction of the maximum value of the complimentary oscillation index.

The use of the complimentary oscillation index has proved to provide superior results as compared with the prior peak to peak or peak to base measurement methods. Substantial improvement has been achieved over a wide variety of wave forms with common artifacts.

In the preferred embodiment of this invention, both digital and analog circuitry is used. A pressure sensor generates an analog signal which is calibrated and amplified. The oscillations are passed via a high pass filter and then converted to the digital domain via an analog to digital converter. The digitized data is stored in random access memory (RAM) and operated upon by a software controlled microprocessor circuitry. In the disclosed embodiment, the microprocessor circuitry performs the function of peak detection, determination of the summed complimentary oscillation value, the interval calculation, determination of the complimentary oscillation index, storage of the oscillation envelope and its associated check for smoothness, a single peak and completeness, and ultimately determines the systolic, diastolic and mean pressures. The results of the pressure determinations are presented on a suitable display.

Accordingly, it is an object of this invention to provide a method for reliably determining the blood pressure in a non-invasive manner.

It is a further object to provide a method for measuring blood pressure which is more resilient to artifacts from various sources.

It is an object of this invention to provide a method for measuring blood pressure which is more reliable and consistent with patients with irregular or inconsistent oscillations.

It is a further object of this invention to avoid making repetitive measurements to determine whether an error or artifact was present.

DETAILED DESCRIPTION

Figures 1B, 2:
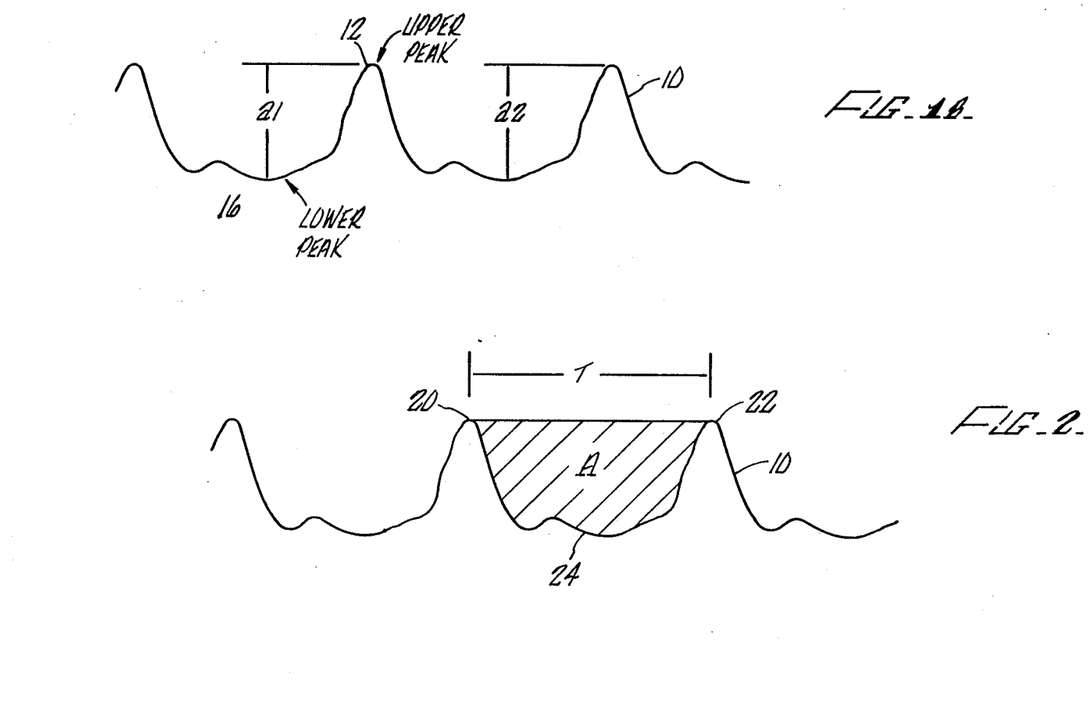
FIG. 1B shows a graphic representation of an oscillation signal with respect to time relative to the Peak to Peak measurement method.
FIG. 2 shows a graphic representation of an oscillation with respect to time relative to the method of calculating the complimentary oscillation index.

A graphic representation of an oscillation signal 10 obtained by conventional techniques is shown in FIG. 2. In accordance with this invention, the complimentary oscillation index is to be determined. In the preferred embodiment, the area bounded by a line extending from a first peak 20 to a second peak 22 and the oscillation signal 24 is computed. This quantity is called the summed complimentary oscillation. This is identified with the letter A on the figure. The time period T between the first peak 20 and the successive peak 22 is determined. The complimentary oscillation index is then computed as follows:

$$\text{complimentary oscillation index} = \frac{\text{summed complimentary oscillation}}{T}.$$

The complimentary oscillation index is to be determined for a variety cuff pressures. In the preferred embodiment, the cuff pressure is set to an initial pressure and the complimentary oscillation index is determined. The complimentary oscillation index and the mean cuff pressure are stored. The cuff pressure is then stepped to the next pressure, the oscillation is measured and the complimentary oscillation index is computed. The new value of the complimentary oscillation index is stored along with the new mean cuff pressure. As the cuff pressures are stepped through, an oscillation envelope is generated.

Figure 3A:
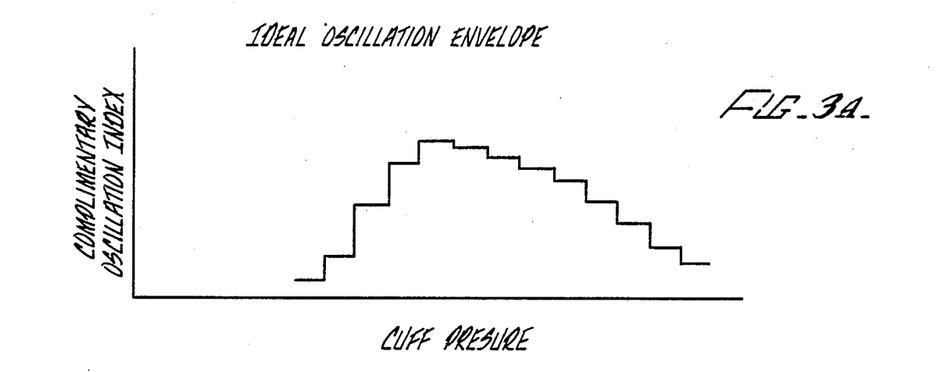
FIGS. 3a, 3b, and 3c show graphical representations of oscillation envelopes, including an ideal oscillation envelope and two corrupted oscillation envelopes.
Figure 3B:
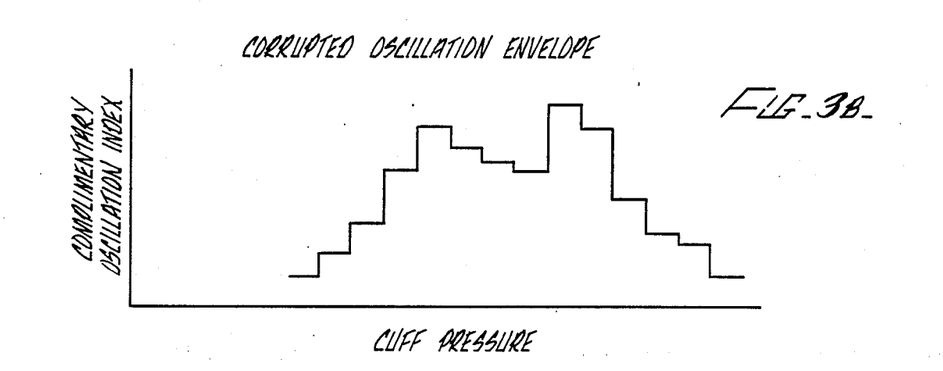
Figure 3C:
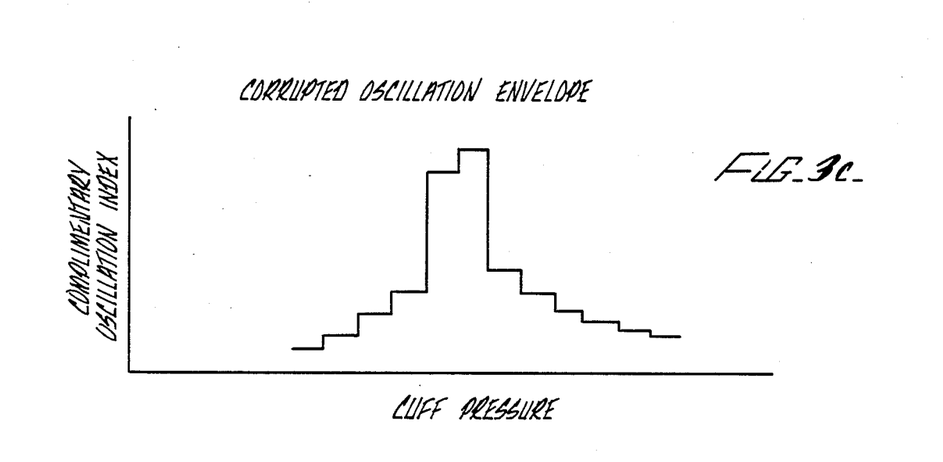

FIG. 3 shows three different oscillation envelopes. The upper figure shows an ideal oscillation envelope, that is, one which exhibits a single peak and the required degree of smoothness. In the case of the ideal oscillation envelope, the mean arterial pressure is taken to be the cuff pressure at which the complimentary oscillation index is a maximum. The systolic and diastolic pressures are taken to be the cuff pressures at which the complimentary oscillation index has decreased to a predetermined fraction or percentage of the maximum value of the complimentary oscillation index. The center and bottom graphs of FIG. 3 show corrupted oscillation envelopes. The middle figure is corrupted as it contains two peaks. The bottom graph is corrupted as it does not exhibit the required degree of smoothness.

By comparing the oscillation envelope with an expected shape of an oscillation envelope it is possible to reset the cuff pressure to the pressure at which the corrupted complimentary oscillation index value was determined. The complimentary oscillation index can be remeasured and utilized with the noncorrupted measurements to determine the blood pressure. In this way, only a single measurement need be made if the value of the complimentary oscillation index conforms with the expected oscillation envelope.

Figure 4A:
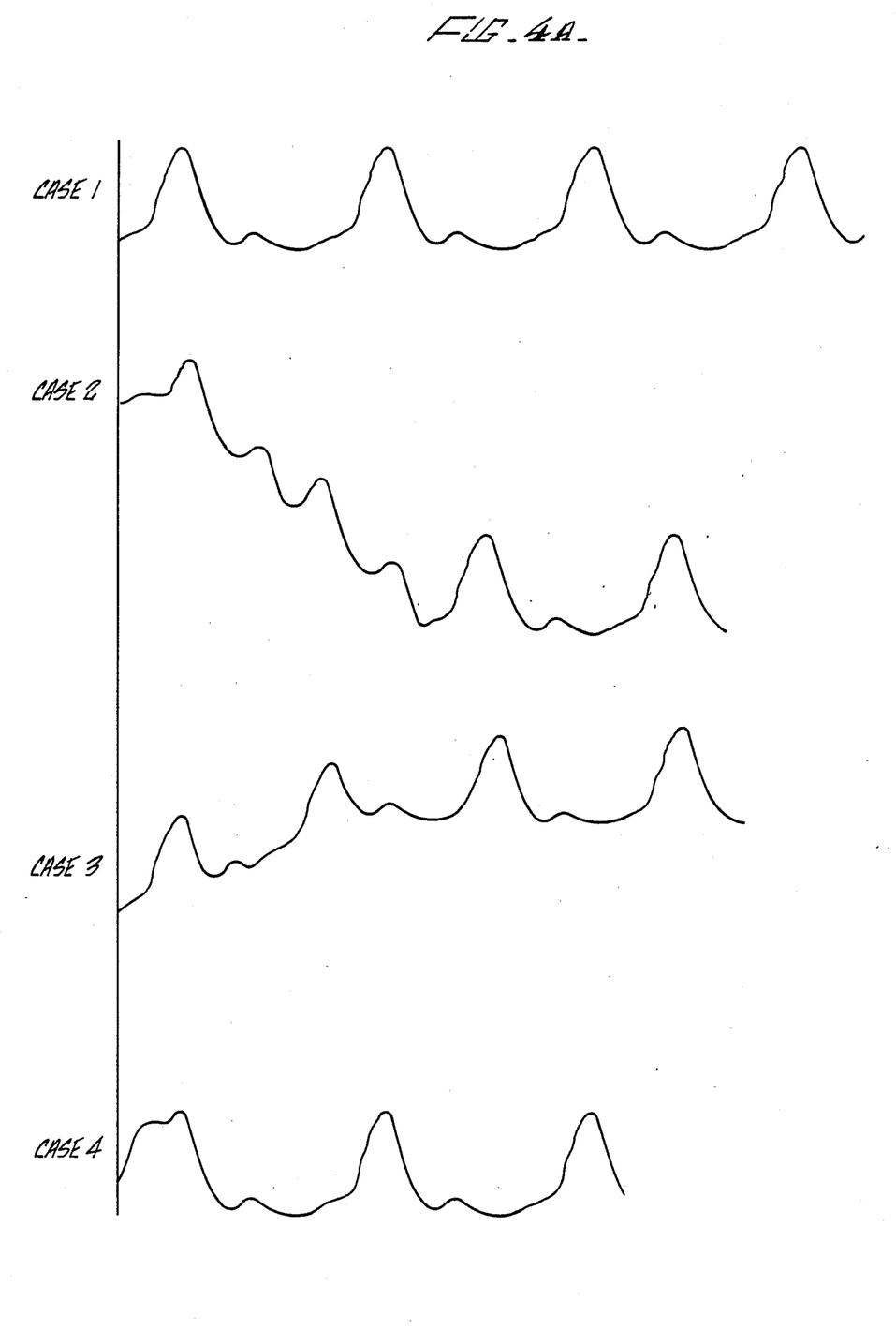
FIGS. 4a and 4b show nine various cases of waveforms, including an ideal wave form plus various artifacts.
Figure 4B:
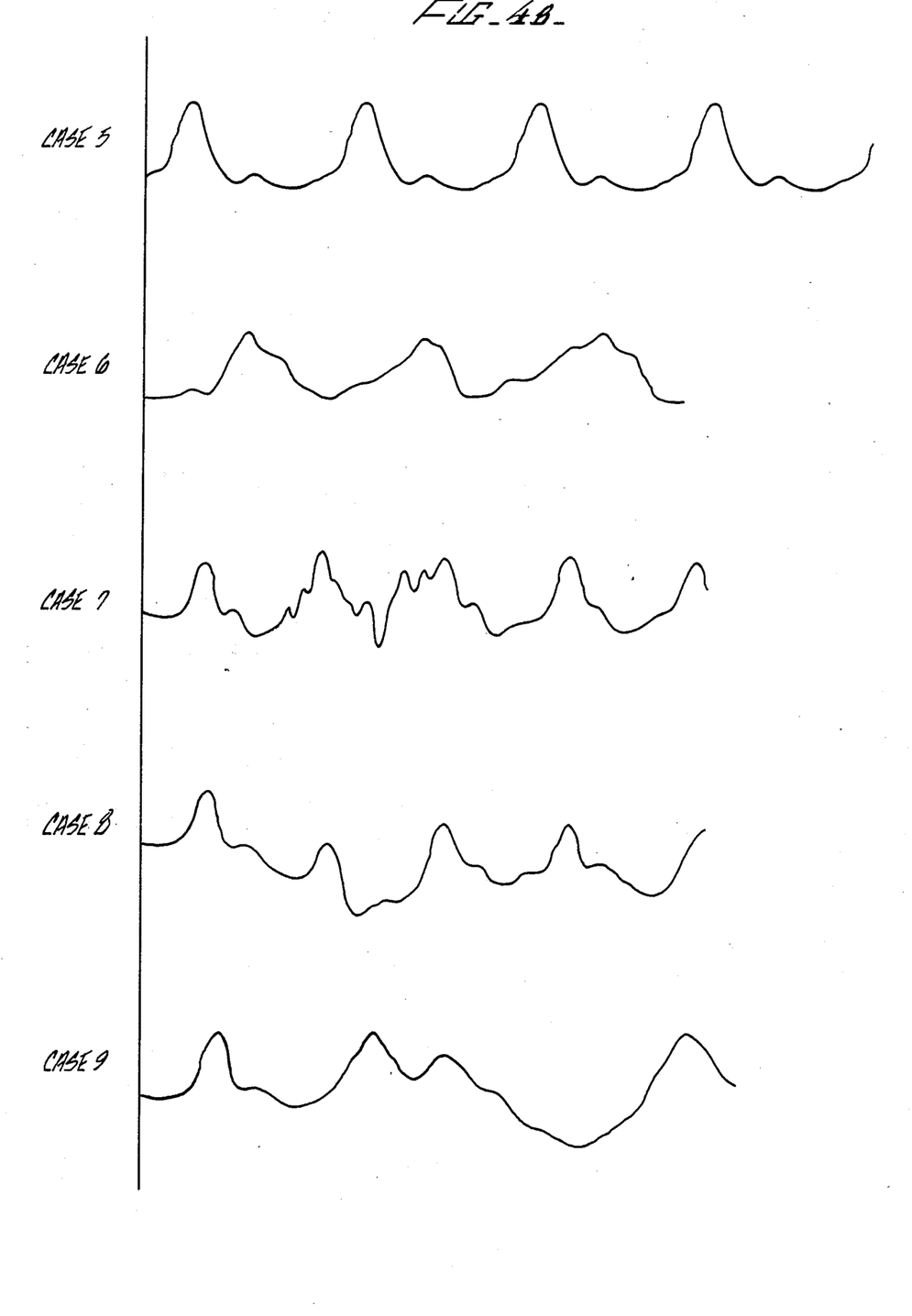

A variety of oscillation patterns are shown in FIG. 4. Case 1 shows an ideal wave form. Case 2 shows the cuff settling in a downward fashion. Case 3 shows a cuff settling in an upward and slow fashion. Case 4 shows a cuff settling in a fast and up manner. Case 5 shows an oscillation signal with an undefined pulse base. Case 6 shows an oscillation signal with a choppy pulse. Case 7 shows an oscillation signal with fast patient movement. Case 8 shows an oscillation signal with slow patient movement. Case 9 shows an oscillation signal of a patient with arrhythmia. The errors in the oscillation magnitude calculation for cases 2 through 9 are compared in Table 1, below. The results are presented for the complimentary oscillation index method, the Base to Peak calculation method and the Peak to Peak calculation method.

TABLE 1

|  | COMPLIMENTARY OSCILLATION INDEX | BASE TO PEAK | PEAK TO PEAK |
|---|---|---|---|
| CASE 2 | 20% | 50% | 50% |
| CASE 3 | 5% | 60% | 60% |
| CASE 4 | 5% | 70% | 5% |
| CASE 5 | 5% | 50% | 5% |
| CASE 6 | 5% | 70% | 5% |
| CASE 7 | 20% | 75% | 25% |
| CASE 8 | 15% | 50% | 60% |
| CASE 9 | 25% | 70% | 60% |

Figure 5:
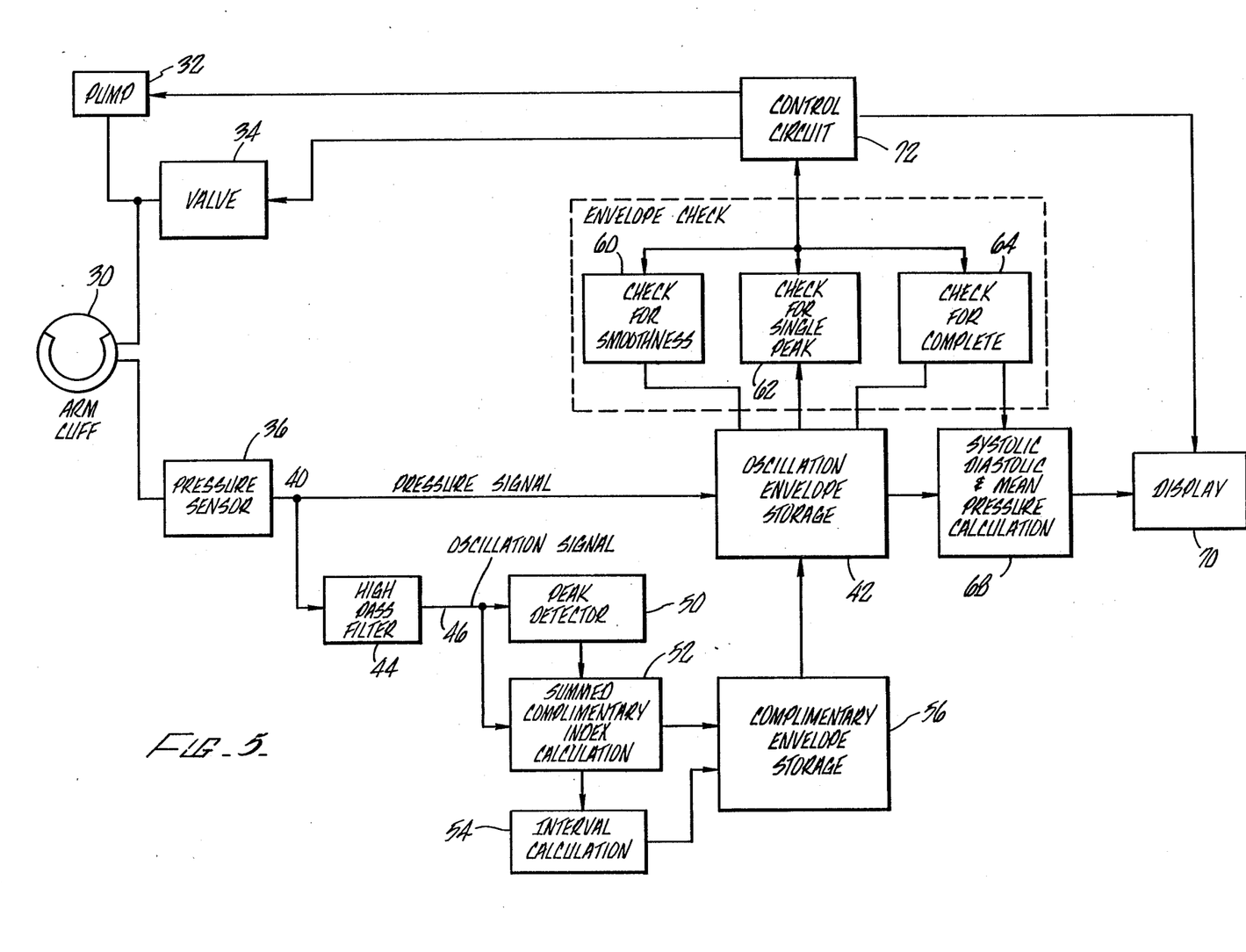
FIG. 5 is a schematic representation of the structural components and functional operations.

FIG. 5 shows an overall schematic representation of the blood pressure measuring system and methodology. An arm cuff 30 is inflated by a pump 32 to the desired cuff pressure. A valve 34 may be used to relieve cuff pressure as necessary. The pressure in the cuff 30 is determined by pressure sensor 36. The pressure sensor 36 generates a pressure signal which is output on line 40. The pressure signal is sent via line 40 to the oscillation envelope storage 42 and is used at least in determining the cuff pressure. The pressure signal is also sent via line 40 to a high pass filter 44 which passes the oscillation signal on line 46. The oscillation signal is used for the function of peak detection as represented by box 50 and for the function of determining the summed complimentary oscillation value as represented by the box 52. This information is also used for interval calculation as represented by the box 54. The complimentary oscillation index calculation is performed using the inputs of the summed complimentary oscillation index and interval calculation. The complimentary oscillation index result is provided to the isolation envelope storage 42.

The information in the oscillation envelope storage 42 is subject to envelope checks. In the preferred embodiment, the oscillation envelope is checked for smoothness as indicated by box 60, checked for a single peak as indicated by box 62 and checked for completeness as indicated by box 64. When the contents of the oscillation envelope storage 42 have passed the envelope check, the systolic, diastolic and mean pressure calculation is done as represented by box 68. The results are presented on a display 70. The operation of the unit is under control of a control circuit 72.

Figure 6:
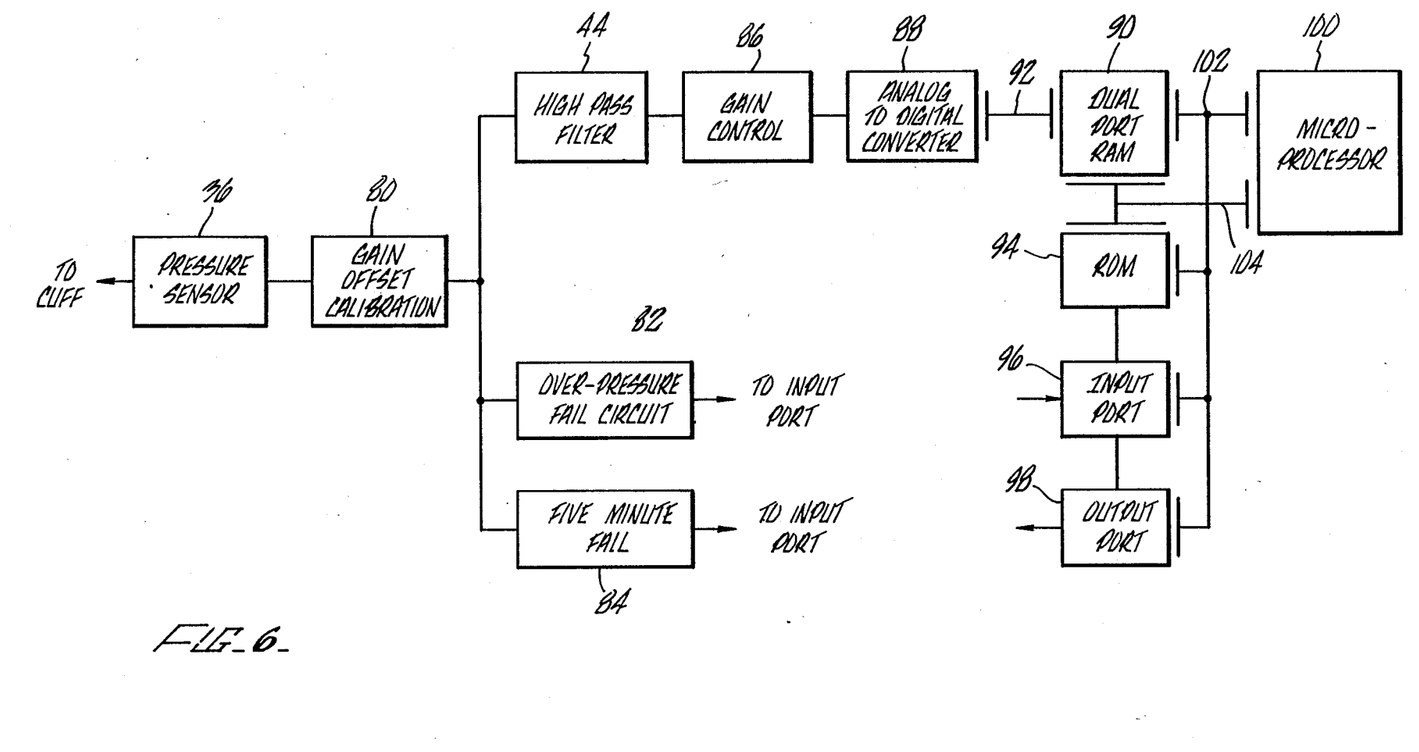
FIG. 6 is a schematic representation of hardware components used in the preferred embodiment.

The hardware circuitry of the preferred embodiment is shown in FIG. 6. The pressure sensor 36 is connected to the arm cuff (not shown). The output of the pressure sensor is amplified and offset in a gain and offset calibration circuit 80. This signal is then monitored for two failure conditions. First, a failure interrupt is indicated if the cuff pressure exceeds 275 mm Hg. Second, an interrupt condition exists if the cuff pressure exceeds 30 mm Hg for longer than 5 minutes.

The signal from the gain and offset calibration circuit 80 is also sent via high pass filter 44 through an amplification stage shown as gain control 86 onto an analog to digital converter 88. The digitized signal is passed over a data bus 92 to a RAM 90. In the preferred embodiment a dual port RAM has been used. The program for operation of the digital aspects of the system is contained in a suitable memory 94, a read only memory being used in the preferred embodiment.

An input port 96 receives input from the analog portions of the circuit. In the preferred embodiment the input signals include an indication that either of the fail conditions, described above, has occurred, or that the analog to digital converter is finished and ready to provide data. An output port 98 provides various control signals to the circuitry, in the preferred embodiment, including signals for activating the pump 32 or valve 34. A microprocessor 100 is used to provide the digital control functions. In the preferred embodiment a Zilog Z80 microprocessor has been used. Appropriate data busses 102 and address bus 104 are used as necessary.

Though the invention has been described with respect to a specific preferred embodiment, many variations and modifications will immediately become apparent to those skilled in the art. This is particularly true with respect to this circuit which may be implemented either in analog circuitry or digital circuitry, or a combination of both as described in the preferred embodiment. Further the digital aspects of a implementation of this invention may be achieved in any variety of software implementations which achieve the functions of this invention. It is further the expectation that the substance of this invention could be implemented in technologies not presently known or existing. Therefore it is the intention that the appended claims be interpreted as broadly as possible in view of the prior art to include all such variations and modifications.

What is claimed is:

1. The method of determining mean arterial pressure comprising the following steps:
    (a) setting the cuff pressure to a first pressure,
    (b) storing the cuff pressure oscillations at the first cuff pressure,
    (c) determining the complimentary oscillation index for the oscillations at the first cuff pressure,
    (d) setting the cuff pressure to a next pressure,
    (e) storing the cuff pressure oscillations at the next pressure,
    (f) determining the complimentary oscillation index for the oscillations at the next pressure,
    (g) repeating steps d through f to establish a complimentary oscillation index envelope, and
    (h) taking the cuff pressure corresponding to the maximum value of the complimentary oscillation index envelope as being the mean arterial pressure.

2. In a method for non-invasive determination of blood pressure, where a value is derived from a signal representative of the pressure oscillations in a cuff, where the value is derived for a plurality of cuff pressures, and where the cuff pressure corresponding to the maximum of the values derived from the pressure oscillations is taken to be the mean arterial pressure, the improvement comprising using as the value the complimentary oscillation index which is defined to be the area bounded by a line connecting successive peaks in the signal and the signal beneath the line, divided by the time between peaks.

3. An automatic blood pressure reading device comprising:
   means for calculating the complimentary oscillation index for a plurality of cuff pressures,
   means for storing the corresponding complimentary oscillation index and cuff pressure, and
   means to determine the maximum value of the complimentary oscillation index.

4. The automatic blood pressure reading device of claim 3 wherein the means for calculating the complimentary oscillation index further includes,
   means for determining the summed oscillation index and the time between pulses.

5. The automatic blood pressure reading device of claim 3 further including means to compare the corresponding complimentary oscillation index and cuff pressure to an oscillation envelope.

6. A method for discriminating for artifact determination in a blood pressure measurement system employing the oscillometric method, comprising the steps of:
   generating a complimentary oscillation index envelope,
   comparing the complimentary oscillation index envelope with the expected shape of the oscillation envelope,
   regenerating any points of the complimentary oscillation index envelope which do not conform to the expected shape of the oscillation envelope.

7. A method for correcting an oscillation envelop in the oscillometric blood pressure measurement technique, comprising the steps of:
   (a) generating a complimentary oscillation index envelope,
   (b) checking the complimentary oscillation index envelope for smoothness and the presence of a single peak, and
   (c) remeasuring the complimentary oscillation index at cuff pressures where the oscillation envelope does not meet either or both of the requirements of step b.

* * * * *